United States Patent
Patel

(10) Patent No.: US 7,297,246 B2
(45) Date of Patent: Nov. 20, 2007

(54) ELECTROKINETIC PUMP

(75) Inventor: Kamlesh D. Patel, Dublin, CA (US)

(73) Assignee: Sandia Corporation, Livermore, CA (US)

(*) Notice: Subject to any disclaimer, the term of this patent is extended or adjusted under 35 U.S.C. 154(b) by 651 days.

(21) Appl. No.: 10/830,773

(22) Filed: Apr. 22, 2004

(65) Prior Publication Data

US 2005/0236272 A1 Oct. 27, 2005

(51) Int. Cl.
*F04F 11/00* (2006.01)
*G05D 7/06* (2006.01)

(52) U.S. Cl. .................. 204/600; 417/48; 422/100

(58) Field of Classification Search ............... 29/592.1; 204/450, 600; 417/48; 422/100
See application file for complete search history.

(56) References Cited

U.S. PATENT DOCUMENTS

| 4,101,460 | A | | 7/1978 | Small et al. |
| 5,532,279 | A | | 7/1996 | Barett et al. |
| 6,632,655 | B1 | * | 10/2003 | Mehta et al. ............ 435/288.5 |
| 2004/0223880 | A1 | * | 11/2004 | Gjerde et al. ................. 422/70 |
| 2005/0230080 | A1 | * | 10/2005 | Paul et al. ..................... 165/47 |

FOREIGN PATENT DOCUMENTS

WO WO 99/16162 4/1999

OTHER PUBLICATIONS

Liu, Yan; Joseph C. Fanguy, Justin M. Bledsoe; Charles S. Henry; Dynamic coating using polyelectrolyte multilayers for chemical control of electroosmotic flow in capillary electrophoresis microchips; Dec. 15, 2000; Analytical Chemistry; vol. 72; pp. 5939-5944.*
Pumera, M.et al., Gold Nanoparticle-enhanced Microchip Capillary Electrophoresis, Anal. Chem., 2001, 5625-5628, 73.
Murrihy, J., et al., Ion Chromatography On-chip, J. Chromatography, 2001, 233-238, 924.
Yan Liu, et al., Dynamic Coating Using Polyelectrolytes Multilayers for Chemical Control of Electroosmotic Flow in Capillary Electrophoresis Microchips, Anal. Chem., 2000, 5939-5944, 72.
Reyes, D., et al., Micro Total Ananlysis Systems 1. Introduction, Theory and Technology, Anal. Chem., 2002, 2623-2636, 74.

* cited by examiner

*Primary Examiner*—Kaj K. Olsen
(74) *Attorney, Agent, or Firm*—Donald A. Nissen

(57) ABSTRACT

A method for altering the surface properties of a particle bed. In application, the method pertains particularly to an electrokinetic pump configuration where nanoparticles are bonded to the surface of the stationary phase to alter the surface properties of the stationary phase including the surface area and/or the zeta potential and thus improve the efficiency and operating range of these pumps. By functionalizing the nanoparticles to change the zeta potential the electrokinetic pump is rendered capable of operating with working fluids having pH values that can range from 2-10 generally and acidic working fluids in particular. For applications in which the pump is intended to handle highly acidic solutions latex nanoparticles that are quaternary amine functionalized can be used.

8 Claims, 3 Drawing Sheets

ELECTROKINETIC PUMP

STATEMENT OF GOVERNMENT INTEREST

This invention was made with Government support under contract No. DE-AC04-94AL85000 awarded by the U.S. Department of Energy to Sandia Corporation. The Government has certain rights in the invention.

CROSS-REFERENCE TO RELATED APPLICATIONS

Not applicable.

FIELD OF THE INVENTION

This invention is directed generally to a method for altering the surface charge and surface area of a particle bed and particularly to an electrokinetic pump configuration wherein nanometer-size particles are bonded to the surface of the particles comprising the stationary phase thereby improving the efficiency and operating range of these pumps. By functionalizing the nanometer-size particles the electrokinetic pump is rendered capable of operating with working fluids having pH values that can range from 2-10 generally and acidic working fluids in particular.

BACKGROUND OF THE INVENTION

Electrokinetic pumps are capable of delivering fluid in the sub-microliter per minute range at pressures in excess of 5000 psi and thus have been found to be useful for fluid dispensing/metering applications in microfluidic devices, high pressure liquid chromatography systems and microanalysis systems generally.

An electrokinetic pump comprises an apparatus for converting electric potential to hydraulic force. An electrokinetic pump, such as described in U.S. Pat. Nos. 6,013,164 and 6,019,882 to Paul and Rakestraw, typically consists of at least one duct or channel, that can be a capillary channel or microchannel that forms a fluid passageway having an inlet and an outlet. The capillary duct or channel contains an electrolyte and has a porous stationary phase or substrate typically comprising a nonporous dielectric medium disposed therein between one or more pairs of spaced electrodes. The porous stationary phase can include small nonporous particles, high surface area structures fabricated within the microchannel, or microporous materials such as monolithic polymer networks. An electric potential is applied between the spaced electrodes in contact with electrolyte, or pump fluid, that can be an aqueous or an organic liquid or mixtures thereof, to cause the electrolyte to move in the microchannel by electroosmotic flow and generate a pressure whose magnitude depends on the Darcy permeability of the fluidic channels downstream of the pump. Pump performance in terms of pressure generated per volt of applied electric potential is determined by composition of the porous dielectric material, the composition of the stationary phase and geometry as well as the properties of the electrolyte.

At the interface between a charged solid and an electrolyte solution an electrochemical double layer is formed and the mobile (diffuse) component of the double layer moves in response to the force generated by an externally applied electric field giving rise to electroosmotic flow.

It has long been recognized in the separations art that in capillary-based devices the zeta ($\zeta$) potential plays a strong role in consistency of electroosmotic flow velocity and the consequent effect on separation efficiency as a result of nonuniform flow in capillary channels (Liu et al. *Anal. Chem.*, 2000, 72, 5939-5941. In the case of electrokinetic pumps, the material comprising the capillary channel walls affects the $\zeta$ potential and maximizing the $\zeta$ potential will maximize pressure, flow rate, and pump performance. Silica surfaces have high wall $\zeta$ potentials at neutral pH and above, and are a common material choice. However, these high energy surfaces can interact with and adsorb many compounds, notably bases. Moreover, the use of silicon dioxide materials in separation systems is further restricted due to the chemical stability of these substrate materials. At pH values greater than about 7 the dissolution rate of silicon dioxide materials increases due to the general weakness of the Si—O—Si bond.

In an attempt to lower costs and overcome the disadvantages of glass and quartz microchips as well as improve electroosmotic flow and thus improve separations efficiency, a variety of different capillary channel materials has been proposed such as polystyrene, poly-(ethylene terphthalate glycol) and fluorocarbons. In addition, a wide variety of channel wall coatings, such as zirconia particles, sulfonic acid groups bonded to silica and quarternary amine groups bonded to silica have been created (Reyes et al., *Anal. Chem.*, 2002, 74, 2623-2636 and references cited therein). However, these channel wall surface modifications display problems such as limited lifetimes, surface contamination, surface charge neutralization and complex fabrication methods. Moreover, many of the surface modifications either degrade under extreme conditions such as very high or low pH or only operate effectively over a limited pH range.

Prior attempts to fabricate positively charged pumping media with zirconia particles, and sulfonic acid groups or quaternary amine groups bonded to silica channel surfaces have failed to produce reliable and robust pumps. Each display problems with limited lifetime, surface contamination, surface charge neutralization, and fabrication complexity.

Polymer monolithic materials have been employed as the stationary phase in electrokinetic pumps, cf. U.S. patent application Ser. No. 09/796,762, Castable Three-dimensional Stationary Phase for Electric Field-driven Applications, filed Feb. 28, 2001 now U.S. Pat. No. 6,846,399.These materials are potentially attractive as stationary phase materials, in particular, because they can be fabricated with charged sites within the polymer structure, thereby providing desired the $\zeta$ potential. However, it has been found that EK pumps fabricated with polymer monoliths containing quaternary amine ($NR_4^+$) charged groups can suffer from efficiency losses likely due to relatively low surface charge density and $\zeta$ potential, an overly broad distribution of pore sizes, lesser structural integrity of the polymer relative to more robust stationary phase materials such as silica, and damage by capillary forces if the polymer monolith is dried after fabrication, and combinations thereof.

SUMMARY OF THE INVENTION

Accordingly, the present invention is directed to an electrokinetic pump (EKP) wherein the stationary phase comprises a nonporous dielectric material, preferably silica particles to which nanometer-size particles are fixedly attached. Most commonly, attachment is by electrostatic attraction, however, attachment can also be by chemical or physical means. The nanometer particles can be selected from any material including, but not limited to, polymer particles, colloidal metal particles, and metal oxide particles. Latex particles are particularly preferred because they can be readily functionalized to be positively or negatively charged.

By functionalizing the nanometer-size particles a zeta potential surface can be created that can improve the pumping efficiency of the EKP. In particular, by the use of quaternary amine ($NR_4^+$), or lower substituted amines ($NR_xH_y^+$), functionalized silica beads it is possible to produce an EKP that will function effectively at pH values of 4 or less. The present invention possesses several advantages for the fabrication of an EKP. By being able to employ packed silica beads as the stationary phase, a configuration heretofore impossible for pumps designed to operate at low pHs because the native silica surface will only function effectively at pH values greater than about 7, it is now possible to take advantage of the high structural integrity of packed silica beds. When combined with particle immobilization techniques disclosed herein it is possible to produce hydraulic pressure greater than about 5000 psi with highly acidic solutions. Moreover, packed silica beads having themselves a very narrow particle size distribution produce a porous stationary phase structure having a very narrow pore size distributions that imparts high pumping (energy conversion) efficiency. Further, a dense coating of nanometer-size particles on the surfaces of silica substrate particles provides a greater surface area than the underlying silica particles themselves thereby providing an advantageously larger surface charge and zeta potential than bare silica surfaces or comparable polymer structures containing quaternary amine functional groups. A large zeta potential further enhances pumping efficiency. High pumping efficiency is desirable to avoid large power dissipation in microfluidic devices, to avoid excessively large current flow through the EKP that can cause deleterious concentration polarization at the electrodes and the microporous medium, and to avoid excessive Joule heating of the solution that can cause deterioration of the pump material, the working fluid or cause the pump to fail due to fluid vaporization.

DETAILED DESCRIPTION OF THE INVENTION

Figure 1A:
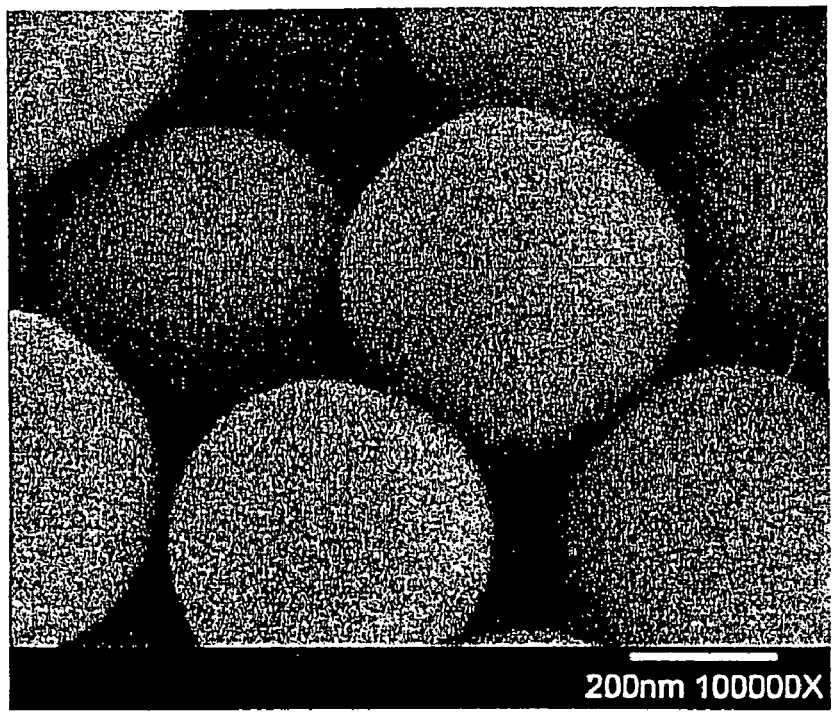
FIGS. 1A and 1B are scanning electron micrographs (SEM) of a packed bed of bare silica particles (1A) and coated with functionalized latex particles (1B).

The invention is directed generally to an electrokinetic pump (EKP) configuration in which nanometer-size particles are fixedly attached to a support surface, that can be the particles comprising a stationary phase, thereby providing means for altering the surface area as well as the net surface charge (zeta potential) of the stationary phase to improve pump efficiency of an EKP. By functionalizing the nanometer particles it is possible to produce an EKP for highly acidic electrolytes as well as other electrolyte compositions.

As discussed above, an EKP typically consists of a capillary channel or microchannel that forms a fluid passageway having at least one inlet and an outlet. The capillary channel or duct contains an electrolyte and has a porous stationary phase or substrate comprising a nonporous dielectric medium disposed therein between one or more pairs of spaced electrodes. The porous dielectric medium can include small nonporous particles, high surface area structures fabricated within the microchannel, or microporous materials such as monolithic polymer networks. Being a microporous structure, the stationary phase has a high flow resistance. Moreover, because of the presence of ionizable surface sites a zeta potential is produced between the particles comprising the porous dielectric medium and the intervening electrolyte. Thus, the zeta potential of the particle/electrolyte interface can be manipulated by changing the surface properties of the particles comprising the stationary phase. The invention relates to changing the surface properties of a stationary phase to affect the zeta potential and thereby improve the efficiency of an EKP that can be subjected to widely different (very acidic or very basic) electrolyte compositions that cannot be tolerated by prior art EK pumps.

Throughout the specification of the invention the terms "channel", "microchannel", "capillary" and "capillary channel" will be used interchangeably and synonymously and typically refer to fluid flow channels whose diameter is in the range of about 5 to 100 µm. The term "nanoparticle" is synonymous for the phrase "nanometer-size particle", i.e., a particle having a diameter in the range of about 1-1000 nm. The term "functionalization" as used herein means the process of adding a functional group(s), such as a quaternary amine or lower substituted amines, to a nanoparticle in order to produce a desired effect upon the zeta potential or surface charge of a nanoparticle and/or the result thereof.

While the discussion below will be directed generally to electrokinetic pumps employing capillary channels, the invention described herein is not limited to these systems but can be useful in larger free-standing pump systems such as that described in co-pending patent application Ser. No. 10/848,201 entitled "High Pressure Microhydraulic Actuator", filed May 17, 2004, incorporated herein in its entirety.

The example below, illustrating one aspect of the invention, is provided as an aid to understanding the invention better. In this embodiment of the invention, quaternary amine functionalized nanometer-size spherical latex particles are fixedly attached by electrostatic attraction to the spherical silica particles that comprise the stationary phase in an EKP. Electrostatic attraction arises not only from the size of the nanoparticles but also from the fact that since the $NR_4^+$ functionalized nanoparticles have a strong positive charge they irreversibly bind to multiple negatively charged silanol groups on the surface of the silica particle matrix, strongly attaching the nanoparticles in place.

At a pH below the pKa of silanol groups (pKa<4) the remaining silanol groups not provided with attached functionalized nanoparticles will be protonated. The net result will be a positive surface charge at which counterbalancing anions will form a double layer in solution. As will be shown below, EK pumps provided with a quaternary amine functionalized stationary phase are capable of pumping acid solutions, generating pressures greater than 5000 psi and flow rates in the nanoliter to microliter range.

EXAMPLE

A slurry of 0.5 µm diameter silica particles was pumped into a 150 µm i.d./360 o.d fused silica capillary provided with a temporary retaining frit. While in the method illustrated here the silica particles are pumped into a capillary tube, other methods know in the art for filling capillary tubes with particulate slurries can also be used, such as that disclosed in U.S. Pat. No. 6,444,150, incorporated herein in its entirety. Pressure (≈30 kpsi) was applied to the slurry in order to build the densely packed bed of particles necessary to form a stationary phase.

Art recognized methods of retaining particle beds such as the use of frits can be cumbersome and difficult both to fabricate as well as maintain open porosity. A preferred method of retaining particle beds is to immobilize the particle bed by an alkoxysilane nanogluing procedure such as that described by Chirica and Remcho (*Electrophoresis*, 20(1), 50-56, 1990). This novel procedure uses a tetraethylorthosilicate (TEOS) or tetramethylorthosilicate (TMOS) to attach individual particles to each other and to capillary walls creating a monolithic-like structure. This procedure is well suited for EK pumps and removes the need for frits.

Briefly, the nanogluing process involves pretreating a packed capillary column (≈12 cm in length) by flushing with a 1 N NaOH solution. Following the NaOH flushing step, the column was flushed with a 1:20 (v/v) solution of acetic acid. Any residual liquid was removed, preferably by evaporative drying. When the packed bed was completely dry a freshly prepared immobilization solution comprising 1.2 mL of TEOS or TMOS and 1.5 mL of acetic acid solution (1:20 (v/v)) is mixed with 4 mL ethanol. Prior to introducing this mixture, the column and any ancillary reservoirs were flushed with ethanol to ensure complete removal of any residual water. Following this step, about 3-4 column volumes of the immobilization solution were passed through the packed column. Typically this step required the application of pressure, generally about 8-10 kpsi. The treated column was typically cured at room temperature for about 2-3 hours and then at 65° C. for about 12 hours.

Following the step of immobilizing the particle bed comprising the stationary phase, a neat solution of $NR_4^+$ functionalized nanoparticles was flushed through the immobilized particle bed for approximately 20-30 minutes at a pressure of about 3000 psi. The solution comprised a mixture of the functionalized nanoparticles and a carrier liquid. For thoroughness, the nanoparticle solution was flushed in a similar manner for a second time in the opposite direction. Although it was not necessary for successful functioning of the invention, it was found desirable to gently warm the filled capillary tube about 5-10° C. above ambient temperature, during the flushing process. Finally, the filled capillary was warmed to about 60° C. to remove the carrier liquid.

While in the example above functionalized nanoparticles were used to cover the silica particles comprising the particle bed or stationary phase, it is understood that non-functionalized nanoparticles could also be used to increase the surface area of the stationary phase thereby improving EKP efficiency. Further, the use of other nanoparticles is contemplated by this invention including polymer particles, colloidal metal particles and metal oxide particles both functionalized and unfunctionalized.

Figure 1B:
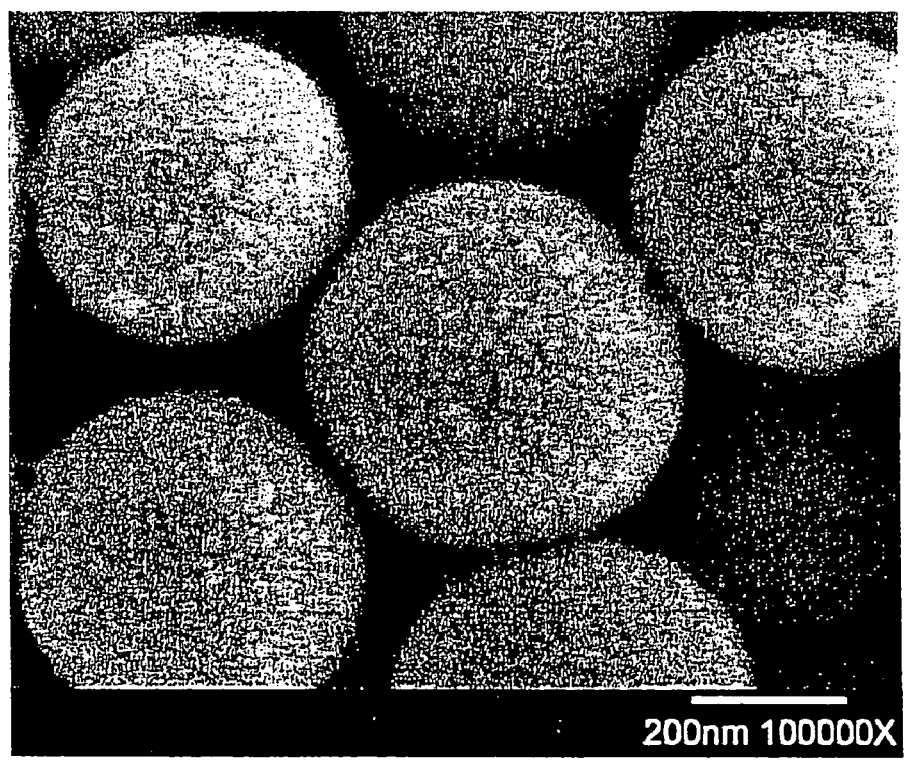

FIG. 1A is a scanning electron micrograph (SEM) of the 0.5 μm silica particles that comprise the particle bed stationary phase in the example above prior to flushing with the functionalized nanoparticle solution. FIG. 1B is a SEM of the same silica particle bed subsequent to flushing with a solution of $NR_4^+$ functionalized latex nanoparticles. Comparing the two micrographs it can be readily seen (FIG. 1B) that the silica particles comprising the stationary phase are uniformly covered with nodules, measuring about 15 nm in diameter, that comprise the functionalized latex particles.

Figure 2:
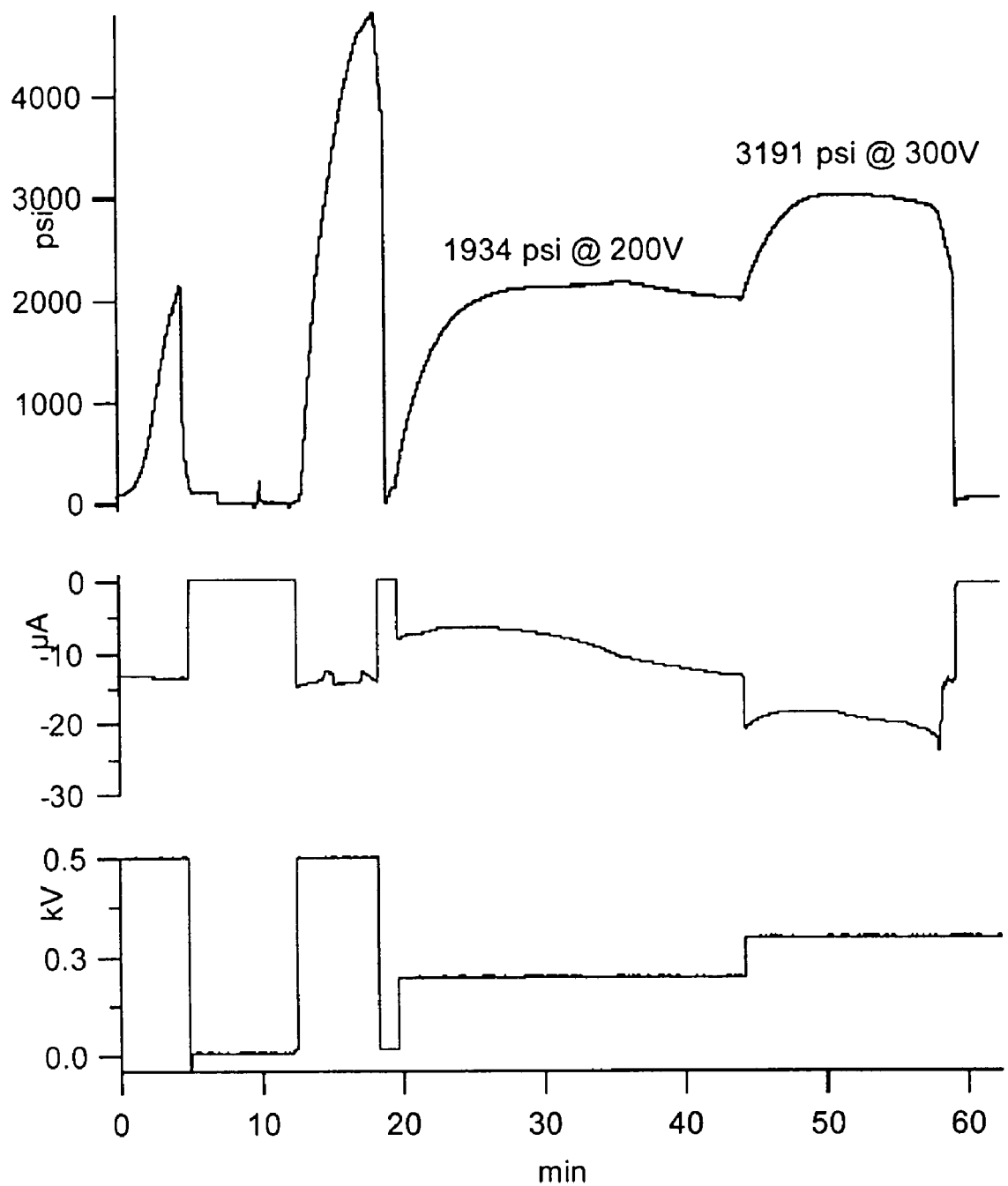
FIG. 2 illustrates the performance of an EKP employing $NR_4^+$ functionalized latex nanoparticles.
Figure 3:
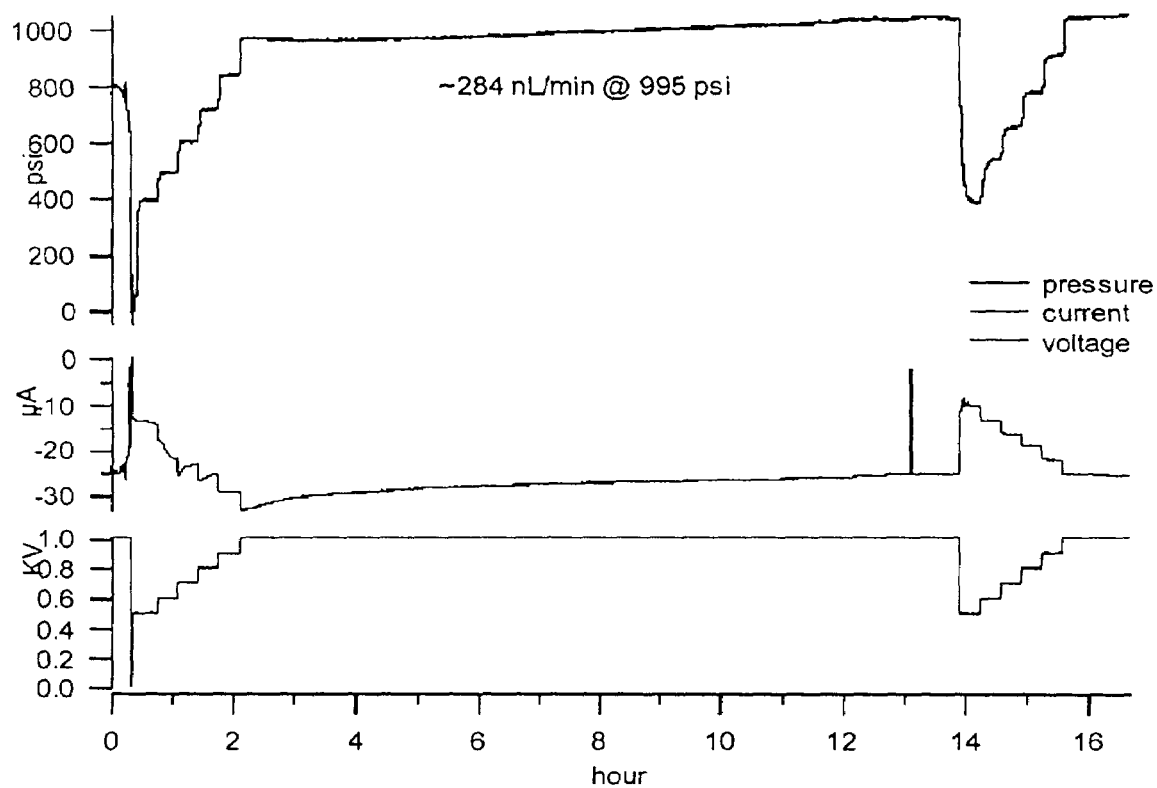
FIG. 3 shows a long duration test of an EKP acid pump.

That an EKP fabricated as described above can effectively pump an acid solution is illustrated in FIG. 2. Here, a formic acid solution (0.05% v/v) is used as the pumping fluid. With only 300 V applied a pressure of nearly 3000 psi was achieved. An additional criterion in evaluating the suitability of these EK pumps is the robustness of functionalized silica bead stationary phase to an acid solution. FIG. 3 shows a long duration EKP test of a pump having a stationary phase comprising $NR_4^+$ functionalized latex beads attached to individual silica beads that form the stationary phase. The solvent is a 5 mM formic acid solution (pH=3.72). At 500 V applied a constant pressure of 285 psi, corresponding to a fluid flow rate of 81 nL/min, was maintained for 800 min.

I claim:

1. An electrokinetic pump, comprising:
   a) a microchannel having at least one fluid inlet and at least one fluid outlet and a porous dielectric material comprising a stationary phase disposed in said microchannel, wherein the stationary phase comprises a bed of nonporous particles and wherein the surfaces of the nonporous particles have nanoparticles fixedly attached thereto;
   b) an electrolyte contained within said microchannel and in communication with the nonporous dielectric material;
   c) spaced electrodes in contact with said electrolyte; and
   d) means for applying an electric potential to said spaced electrodes.

2. The electrokinetic pump of claim 1, wherein nanoparticles include polymer particles, colloidal metal particles and metal oxide particles.

3. The electrokinetic pump of claim 1, wherein the nanoparticles are functionalized nanoparticles.

4. The electrokinetic pump of claim 3, wherein the functionalized nanoparticles are functionalized latex nanoparticles.

5. The electrokinetic pump of claim 4, wherein the functionalized latex nanoparticles include quaternary amine functionalized latex nanoparticles.

6. The electrokinetic pump of claim 1, wherein the nonporous particles include silica particles.

7. An electrokinetic pump for pumping acid solutions, comprising:
   a) a microchannel having at least one fluid inlet and at least one fluid outlet and a porous dielectric material comprising a stationary phase disposed in said microchannel, wherein the stationary phase comprises a bed of nonporous particles and wherein the surface of the nonporous particles have quaternary amine functionalized latex nanoparticles fixedly attached thereto;
   b) an acid electrolyte contained within said microchannel and in communication with the nonporous dielectric material;
   c) spaced electrodes in contact with said electrolyte; and
   d) means for applying an electric potential to said spaced electrodes.

8. The electrokinetic pump of claim 7, wherein the nonporous particles are silica particles.

* * * * *